United States Patent [19]

Rosen et al.

[11] Patent Number: 5,227,369
[45] Date of Patent: Jul. 13, 1993

[54] COMPOSITIONS AND METHODS FOR INHIBITING LEUKOCYTE ADHESION TO CNS MYELIN

[75] Inventors: Steven Rosen; Kun Huang, both of San Francisco; Mark Singer, Berkeley, all of Calif.; Joyce Geoffroy, late of Burnham, Ill., by Dolores T. Siniawski, administratrix

[73] Assignee: The Regents of the University of California, Oakland, Calif.

[21] Appl. No.: 727,280

[22] Filed: Jul. 11, 1991

[51] Int. Cl.$^5$ .............. A61K 31/70; A61K 31/715; A61K 39/395

[52] U.S. Cl. ........................ 514/23; 514/903; 514/885; 514/2; 514/3; 514/8; 514/4

[58] Field of Search .............. 514/903, 23, 885, 2, 514/3, 4

[56] References Cited

U.S. PATENT DOCUMENTS

| | | | |
|---|---|---|---|
| 4,294,818 | 10/1981 | McMichael et al. | 436/534 |
| 4,618,601 | 10/1986 | Chazot et al. | 514/903 |
| 4,752,563 | 6/1988 | Kortright et al. | 435/962 |
| 4,818,686 | 4/1989 | Kortright et al. | 435/962 |
| 4,839,276 | 6/1989 | Adolfsen et al. | 435/962 |
| 4,935,343 | 6/1990 | Allison et al. | 435/962 |
| 4,948,726 | 8/1990 | Longoria | 435/962 |
| 4,994,466 | 2/1991 | Sherman et al. | 514/903 |
| 5,036,102 | 7/1991 | Bachynsky et al. | 514/903 |

FOREIGN PATENT DOCUMENTS

| | | |
|---|---|---|
| 153875 | 9/1985 | European Pat. Off. |
| 184040 | 6/1986 | European Pat. Off. |

OTHER PUBLICATIONS

Willenborg, D. O. and Parish, C. R., *J. Immunol.*, 140: 3401-3405 (May 15, 1988).
Willenborg, D. O. et al., *FASEB J.*, 3: 1968-1971 (Jun. 1989).
Glabe, C. G. et al., *Anal. Biochem.*, 130: 287-294 Mar. 1983.
Stoolman, L. M. and Rosen, S. D., *J. Cell Biol.*, 96: 722-729 Mar. 1983.
Gallatin, W. M. et al., *Nature*, 304: 30-34 Jul. 7, 1983.
Stoolman, L. M. et al., *J. Cell Biol.*, 99: 1535-1540 Oct. 1984.
Yednock, T. A. et al., *J. Cell Biol.*, 104: 713-723, 725-731 Mar. 1987.
Lasky, L. A. et al., *Cell*, 56: 1045-1055 Mar. 24, 1989.
Siegelman, M. H. et al., *Science*, 243: 1165-1172 Mar. 3, 1989.
Kishimoto, T. K. et al., *Proc. Natl. Acad. Sci USA*, 87:2244-2248 Mar. 1990.
Imai, Y. et al., *J. Cell. Biol.*, 111: 1225-1232 (Sep. 1990).
Springer, T. A. *Nature*, 346: 425-434 Aug. 2, 1990.
Spertini, O. et al., *Nature*, 349: 691-694 (Feb. 21, 1991).
Kishimoto, T. K. et al., *Science*, 245: 1238-1241 (Sep. 15, 1989).
Watson, S. R. et al., *Nature*, 349: 164-167 Jan. 10, 1991.
Coombe, D. R. and Rider, C. C., *Immunol. Today*, 10:289-291 Apr. 1989.
Watson, S. R. et al., *J. Cell. Biol.*, 110: 2221-2239 Jun. 1990.
Jutila, M. A. et al., *Transplantation*, 48: 727-731 Nov. 1989.
Jutila, M. A. et al., *J. Immunol.*, 143: 3318-3324 Nov. 15, 1989.
Kuttner, B. J. and Woodruff, J. J., *J. Immunol.*, 122: 1666-1671 May 1979.

Primary Examiner—Ronald W. Griffin
Attorney, Agent, or Firm—Townsend and Townsend

[57] ABSTRACT

The present invention provides pharmaceutical compositions and methods for treating demyelinating diseases. The compositions comprise a blocking agent which inhibits LHR-mediated binding of leukocytes to myelin.

13 Claims, No Drawings

COMPOSITIONS AND METHODS FOR INHIBITING LEUKOCYTE ADHESION TO CNS MYELIN

This invention was made with support under Grant Nos. GM23547 and AR0684 awarded by the National Institute of Health. The Government has certain rights in this invention.

BACKGROUND OF THE INVENTION

The present invention relates to pharmaceutical compositions and methods for treating demyelinating diseases. In particular, the invention relates to treatment using agents which inhibit leukocyte adhesion mediated by lymphocyte homing receptors (LHR).

Recent work has established that specialized cell surface receptors (termed here selectins or LECCAMs) on endothelial cells and various circulating cells are involved in a number of intercellular interactions. LHR (also known as $gp90^{MEL}$, $gp100^{MEL}$, $gp110^{MEL}$, Mel-14 antigen, Leu8 antigen, TQ1 antigen, DREG antigen, LAM-1, selectin 1, LECAM-1 and LECAM-1) is a selectin receptor on the surface of leukocytes and is known to be involved in the adhesive interactions of leukocytes with the endothelial lining of blood vessels. This adhesive interaction is a prerequisite for the movement of leukocytes from the blood to tissue sites where immune reactions and inflammatory reactions occur. LHR is also important for lymphocyte homing from the blood into secondary lymphoid organs.

All selectins share certain structural features, including a lectin-like region which recognizes specific carbohydrate-containing ligands. For a review, of selectin receptors see, Springer, *Nature*, 346:425 (1990), which is incorporated herein by reference. Other selectin receptors are found on endothelial cells and platelets. Endothelial leukocyte adhesion molecule-1 (ELAM-1) is present on endothelial cells and is involved in the recognition of various circulating cells by the endothelium. Granule membrane protein-140 (GMP-140) is present on the surface of platelets and endothelial cells, where it mediates platelet-leukocyte and endothelium-leukocyte interactions.

There is currently an interest in developing highly specific competitive inhibitors of selectin-mediated cellular adhesion. Such inhibitors are useful in therapeutic regimens to treat various selectin-mediated disease responses. In particular, little is known about the role selectins might play in responses other than inflammation and lymphocyte homing. Identification of other interactions involving selectin receptors will open new paths to therapy for other disease processes.

SUMMARY OF THE INVENTION

The present invention concerns pharmaceutical compositions and methods which are useful for treating and diagnosing demyelinating diseases. The claimed pharmaceutical compositions comprise a pharmaceutically acceptable carrier and a blocking agent which inhibits LHR-mediated binding of leukocytes to myelin. The claimed methods use these compositions for treating and diagnosing demyelinating diseases, such as multiple sclerosis.

The blocking agents of the present invention function by selectively binding either LHR or the recognition determinant on myelin. Those blocking agents which selectively bind LHR are typically carbohydrates or compounds which comprise a carbohydrate moiety which selectively binds LHR. Carbohydrates of the present invention include mannose-6-phosphate, fructose-1-phosphate or fragments of fucoidin or the phosphomannan monoester core from *Hansenula hostii* (PPME). Compounds which comprise an LHR-binding moiety include glycolipids, such as sulfatide, and glycoproteins, such as endothelial cell surface glycoproteins. The glycoproteins are preferably an extracellular region of $Sgp^{50}$ or $Sgp^{90}$. The blocking agent may also be an immunoglobulin which reacts with LHR, such as TQ1 and LAM 1.4.

Blocking agents which selectively bind the recognition determinant on myelin are typically isolated LHR, which may be in soluble form or embedded in a lipid membrane. Soluble forms of LHR preferably comprise an LHR component and an immunoglobulin component.

DESCRIPTION OF THE PREFERRED EMBODIMENTS

As discussed above, LHR is known to be involved in a number of physiological responses. For instance, the trafficking of lymphocytes from the blood into secondary lymphoid organs, such as lymph nodes and gut-associated Peyer's patches, is known to be initiated by an adhesive interaction between specialized endothelial cells of high endothelial venules (HEV) and LHRs on lymphocytes. Berg et al., *Immunol. Rev.* 108:5-18 (1989); Duijvestijn and Hamann, *Immunol. Today* 10:23-28 (1989); Woodruff et al., *Ann. Rev. Immunol.* 5:201-222 (1987); Yednock and Rosen, *Adv. Immunol.* 54:313-378 (1989); Stoolman, *Cell* 56:907-910 (1989); Gallatin et al., *Cell* 44:673-680 (1986); Rosen, *Curr. Opin. Cell. Biol.* 1:913-919 (1989), all of which are incorporated herein by reference. In addition, LHR on neutrophils, monocytes, and eosinophils mediates the early interaction of these cells with endothelium of blood vessels at sites of inflammation (Gallatin, et al., *Nature* 304:30 (1983) and Lewinsohn, et al., *J. Immunol.* 138:4313 (1987), which are incorporated herein by reference).

The lectin domain on LHR for lymph nodes in humans and mice was initially inferred based upon the ability of specific phosphorylated monosaccharides, such as mannose-6-phosphate (M6P), and specific polysaccharides to prevent lymphocyte attachment to HEV (Stoolman and Rosen, *J. Cell Biol.* 96:722-729 (1983); Stoolman et al., *J. Cell Biol.* 99:1535-1540 (1984); Yednock et al., *J. Cell Biol.* 104:713-723 (1987); Stoolman et al., *Blood* 70:1842-1850 (1987); Stoolman and Ebling, *J. Clin. Invest.* 84:1196-1205 (1989) all of which are incorporated herein by reference). Notable among the active polysaccharides are PPME (a phosphate-rich mannan core) and fucoidin (a sulfated, fucose-rich polymer). This carbohydrate-binding activity depends on the presence of calcium, which is also required for the attachment of lymphocytes to HEV.

From the lectin nature of LHR, the ligands on lymph node HEV are presumed to bear a carbohydrate-based recognition determinant. Early studies demonstrated that the adhesive sites on peripheral lymph node HEV are periodate sensitive (Rosen et al., *Science* 228:1005-1007 (1985) which is incorporated herein by reference), indicating a requirement for carbohydrate. Subsequently, it was demonstrated that sialidase treatment of HEV, in vitro or in vivo, selectively eliminates lymphocyte attachment to peripheral lymph node HEV but has no effect on the binding to Peyer's patch HEV (Rosen et al., *J. Immunol.* 142:1895-1902 (1989) Which is incorporated herein by reference). In addition, exposure of peripheral lymph node tissue sections to Limax flavus agglutinin, a sialic acid-specific lectin, prevents lymphocyte attachment to HEV (True et al., *J. Cell Biol.* 111:2757-2764 (1990) which is incorporated herein by reference).

The structure and function of selectin receptors has been elucidated by cloning and expression of full length cDNA encoding each of the receptors (see, e.g., Bevilacqua et al., *Science*, 243:1160 (1989) (ELAM-1), Geng et al., 343:757-760 (1990) (GMP 140), and Lasky et al., *Cell* 56:1045-1055 (1989) (LHR) Which are incorporated herein by reference). The extracellular portion of selectins can be divided into three segments based on homologies to previously described proteins. The N-terminal region (about 120 amino acids) is related to the C-type mammalian lectin protein family as described by Drickamer, *J. Biol. Chem.*, 263: 9557-9560 (1988) (which is incorporated herein by reference) that includes low affinity IgE receptor CD23. A polypeptide segment follows, which has a sequence that is related to proteins containing the epidermal growth factor (EGF) motif. Lastly, after the EGF domain are one or more tandem repetitive motifs of about 60 amino acids each, related to those found in a family of complement regulatory proteins.

A basis for the present invention is the discovery that LHR plays a role in mediating binding of leukocytes to myelinated regions of the central nervous system (CNS). The myelin sheath is a layer comprised primarily of lipid and protein which surrounds the axons of neurons in the central and peripheral nervous systems. The sheath acts as an electrical insulator by preventing the transport of ions across the neuron membrane. In the CNS, the myelin sheath is formed from the plasma membrane of oligodendrocytes which envelop the axon.

A number of neurological disorders are the result of demyelination of axons in the CNS. Demyelinating diseases typically involve patchy destruction of the myelin sheath to form cleared regions of the axon referred to as plaques. Typically, the disease is accompanied by an inflammatory response, as well. Demyelinating diseases include multiple sclerosis (MS), acute disseminated encephalomyelitis, acute necrotizing hemorrhagic encephalomyelitis, and HIV associated myelopathy. MS is the most common of the demyelinating diseases and is generally thought to involve autoimmunity, perhaps induced by viral infection. For a brief review of MS and other demyelinating diseases, see, Antel et al., in *Harrison's Principles of Internal Medicine*, 12th ed., Wilson et al. eds, (McGraw Hill, New York), which is incorporated herein by reference.

The evidence provided here shows that LHR plays a role in the pathogenesis of demyelinating diseases such as MS. LHR is a targeting molecule involved in the selective destruction of the myelin sheaths of CNS neurons. Because LHR is expressed by most lymphocytes, regardless of antigen specificity, non-immunogenic responses must be involved in the etiology of these diseases and other conditions such as traumatic injury to the spinal cord. LHR thus mediates association of other leukocytes, such as monocytes, neutrophils, basophils, and eosinophils to myelinated sheaths. These cells may gain entry into the brain or other parts of the CNS (normally a privileged site devoid of leukocytes) through, for example, traumatic injury to the spinal cord. Selective damage then results from a number of mechanisms such as cell-mediated cytotoxicity or from the local release of cytokines, proteases, or free-radicals.

With the discovery of this new role for LHR, agents known to block LHR-mediated adhesion can be used in treating demyelinating disease. The blocking agents of the present invention function either by selectively binding LHR (i.e., substituting for the recognition determinant on myelin) or by selectively binding the recognition determinant on myelin (i.e., substituting for LHR on the leukocyte). Assays which identify compounds able to block LHR-mediated binding can be used to identify a wide range of compounds useful in the present invention. Copending application U.S. Ser. No. 07/695,805, which is incorporated herein by reference, discloses a number of assays useful in identifying such compounds.

Blocking agents of the present invention selectively bind either LHR or the recognition determinant on myelin. Selective binding as used herein refers to specific recognition by one molecule (typically referred to as a receptor) of another molecule (typically referred to as a ligand) by the spatial or polar organization of a recognition determinant on the second molecule. Selective binding is said to occur when the binding affinity between the molecules is sufficiently high. Binding affinity is typically represented by the affinity constant ($K_a$) for equilibrium concentrations of associated and disassociated configurations, i.e., $K_a = [R-L]/[R][L]$ where [R], [L], and [R-L] are the concentrations at equilibrium of the receptor (R), ligand (L) and receptor-ligand complex (R-L), respectively. Under physiological conditions, the affinity constant of a blocking agent of the present invention is typically about $10^4$ to about $10^8$ liters/mole, and preferably about $10^8$ liters/mole or more. One of skill will recognize, however, that binding affinity between two molecules will be influenced by a number of factors such as temperature, pH, ionic strength, and the like.

A number of compounds which selectively bind LHR are useful as blocking agents in the present invention. Thus these compounds act as antagonists to the myelin recognition determinant. As used herein, the recognition determinant is the minimal structure on myelin which selectively binds LHR. Antagonists are compounds which reverse the physiological effect of a ligand or exclude binding of the ligand to a receptor. An antagonist competes directly or indirectly with the ligand for the receptor binding site and, thus, reduces the proportion of ligand molecules bound to the receptor. Typically, an antagonist is the topographical equivalent of the natural ligand and will compete directly with the ligand for the binding site on the selectin. Such a compound is referred to here as a "mimetic." A ligand mimetic is a molecule that conformationally and functionally serves as substitute for the natural ligand recognized by a selectin receptor. Alternatively, if the ligand and the blocking agent can bind the receptor simultaneously, the compound may act non-competitively. A non-competitive inhibitor acts by decreasing or inhibiting the subsequent physiological effects of receptor-ligand interactions rather than by diminishing the proportion of ligand molecules bound to the receptor.

A blocking agent of the present invention which selectively binds LHR is typically a synthetic or naturally-produced biomolecule, such as a carbohydrate (e.g., oligosaccharide) or a glycoconjugate comprising a structure specifically recognized by LHR. Biomolecules as defined here include but are not limited to biologically significant molecules such as amino acids (and their mimetics), oligopeptides, proteins (e.g., glycoproteins and protein hormones), fatty acids, lipids (e.g., glycolipids, phospholipids, sphingolipids and gangliosides, such as $GM_1$, $GM_2$, and the like), steroid hormones, oligosaccharides, polysaccharides, and nucleic acids (e.g., deoxyribonucleic acids and ribonucleic acids). The blocking agent is preferably a relatively small molecule with a molecular weight less than about 10 kD, preferably less than about 5 kD.

A number of carbohydrate-containing compounds which selectively bind LHR are conveniently used as the blocking agent in the present invention. For instance, phosphorylated monosaccharides, such as mannose-6-phosphate and fructose-1-phosphate inhibit lymphocyte attachment to HEV in in vitro cellular assays. Polysaccharides and glycolipids, have also been shown to inhibit in vitro binding of these cells (Stoolman et al., *Blood* 70:1842-1850 (1987); Yednock et al., *J. Cell Biol.* 104:713-723 (1987); and Yednock et al., *J. Cell Biol.*, 104:725-731 (1987), and Imai et al., *J. Cell Biol.* 111:1225-1232 (1990) Which are incorporated herein by reference.

The carbohydrate-containing compounds of the present invention are typically phosphorylated, sulfated, sialylated, and/or fucosylated. One of skill will readily recognize that, using standard techniques (e.g., enzymatic or chemical synthesis) oligosaccharides capable of selectively binding LHR can be prepared. These compounds can then be screened using standard methods (e.g., those in the example section, below) to determine the ability of the carbohydrates to inhibit binding to myelinated sheaths.

Phosphorylated polysaccharides of the present invention include the phosphomannan monoester core from *Hansenula hostii* (PPME). Sulfated polysaccharides include fucoidin, egg jelly fucan and dextran sulfate. Sulfated glycolipids of the invention include sulfatide. Sialylated glycolipids (e.g., gangliosides) include $GM_1$ $GM_2$, $GD_{1a}$ and the like. Typically, fragments which retain LHR-binding ability are used in the present invention. One of skill will readily recognize methods for preparing and assaying the appropriate fragments of these compounds. The fragments will typically have a molecular weight of less than about 10 kD, preferably less than about 5 kD.

Lymph node endothelial cell surface sialylated, sulfated glycoproteins which comprise oligosaccharide biological ligands specifically recognized by LHR can also be used in the present invention. As demonstrated in copending application U.S. Ser. No. 07/695,805, two such glycoproteins, $Sgp^{50}$ and $Sgp^{90}$, have been identified (see, also, Imai et al., *J. Cell Biol.* 113:1213-1221 (1991), which is incorporated herein by reference). Having identified ligand-bearing glycoproteins, one of skill will recognize that a number of modifications of the glycoproteins that do not significantly alter the LHR binding activity are possible. Such modifications include enzymatic or chemical treatment of the proteins to produce fragments that comprise the carbohydrate ligand recognized by LHR. For instance, fragments of the proteins can be obtained by treatment with an appropriate protease such as trypsin, pronase, papain, pepsin and the like.

The fragments of the present invention typically comprise at least a portion of the glycoprotein extracellular region (i.e., that portion which comprises a carbohydrate ligand recognized by LHR and which is outside the transmembrane and intracellular regions). Because the extracellular region substantially lacks the hydrophobic transmembrane region, it is typically water soluble. The extracellular region, however, may also contain sequences from the transmembrane region (less than about 10 amino acids), so long as solubility is not substantially affected.

As used here, a compound comprising the extracellular region includes any compound in which at least a portion of the extracellular region is conjugated to a second moiety. The term also embraces the isolated extracellular region and the isolated full length glycoprotein, or fragment thereof. An isolated compound comprising the extracellular region includes such a compound (e.g., a full length glycoprotein) in other than its native state, that is, not associated with an endothelial cell. For instance, the compound may be recombinantly produced, solubilized from the appropriate cell, or associated with a synthetic lipid membrane, for example, a liposome. Methods for preparing liposomes are well known in the art, see, e.g., Szoka et al., *Ann. Rev. Biophys. Bioeng.* 9:467 (1980), U.S. Pat. Nos. 4,235,871, 4,501,728 and 4,837,028, incorporated herein by reference.

Analysis of the sulfated glycoproteins of the present invention has revealed that the oligosaccharide moieties recognized by LHR are O-linked. Thus, they can be cleaved from the protein backbones by beta elimination and borohydride reduction according to standard techniques (see, e.g., Fukuda, *Meth. Enzymol.* 179:17-29 (1989), which is incorporated herein by reference). Once cleaved, oligosaccharides can be conjugated to any number of other compounds. For instance, they can be conjugated to a biomolecule using standard techniques. Neoglycoproteins, neoglycolipids or cluster glycosides can be prepared based on the carbohydrate chains of the glycoproteins using methods well known in the art (see, e.g., Stowell et al., *Adv. Carb. Chem and Biochem.* 37:225-281 (1980), Childs et al. *Biochem. J.*, 262:131-138 (1989), and Lee et al., *Glycoconjugate J.* 4:317-328 (1987), which are incorporated herein by reference).

The sulfated glycoproteins can be isolated using a number of techniques. For instance, soluble LHR can be used to identify the glycoproteins in a preparation of proteins isolated from endothelial cells. The glycoproteins can be used as they are isolated or they can be modified according to techniques well known in the art. For instance, the extracellular region can be conjugated to a variety of other compounds (e.g., immunoglobulin constant regions) to confer any number of desired characteristics, such as improved solubility, serum half-life and the like. For a description of methods for making novel derivatives of cell surface proteins which comprise immunoglobulin constant regions see, EP Patent Application No. 88309194.4, which is incorporated herein by reference.

Blocking agents which selectively bind LHR can be easily prepared from commonly available starting materials. Biomolecules can be isolated from any natural source, such as animal, plant, fungal, or prokaryotic cells in accordance with standard procedures. For instance, PPME is purified from crude yeast mannan by the method of Slodki et al., *Biochim. Biophys. Acta,*

304:449-456 (1973), which is incorporated herein by reference. Briefly, the phosphomannan is acid hydrolyzed. After neutralization, the phosphomannan core is precipitated and rehydrated in water. Contaminating protein is removed by water:chloroform:butanol extraction. Alternatively, many polysaccharides (such as fucoidin) and glycolipids can be purchased from chemical supply companies, such as Sigma Chemical Co. (St. Louis, Mo.) and Aldrich Chemical Co. (Milwaukee, Wis.).

Many blocking agents are synthetically produced using standard methods. See, e.g., Khadem, *Carbohydrate Chemistry* (Academic Press, San Diego, Calif., 1988), which is incorporated herein by reference, for synthesis of carbohydrates. Methods for synthesizing polypeptides of defined composition are well known in the art (see, Atherton et al. *Solid Phase Peptide Synthesis* (IRL Press, Oxford, 1989) which is incorporated herein by reference).

The blocking agents of the present invention can also be agents which selectively bind the recognition determinant on the myelin sheath. For instance, isolated LHR can be used to block adhesion. The term "isolated LHR" as used herein refers to an LHR molecule, or fragment thereof, in other than its native state, for example, not associated with the cell which normally expresses it. As discussed above, cDNA encoding human LHR has been isolated. Thus, LHR, or fragments thereof, can be recombinantly produced using standard methods well known to those skilled in the art. For a review of standard molecular biological techniques see Sambrook et al., *Molecular Cloning: A Laboratory Manual,* 2d Ed. (Cold Spring Harbor Press, N.Y., 1989), which is incorporated herein by reference. In addition, using standard recombinant DNA techniques, mutations can be induced to obtain proteins with altered amino acid sequences. Typically, substitutions, deletions or additions are introduced which provide desired characteristics. For instance, increased solubility can be achieved by elimination of the hydrophobic transmembrane region of the protein. In addition, soluble chimeric receptors comprising the constant region of an immunoglobulin molecule, termed here LHR-IgG, can also be produced (Watson et al., *J. Cell Biol.* 110 2221-2229 (1990), and Watson et al., *Nature* 349:164-167 (1991) which are incorporated herein by reference). LHR, or fragments thereof, can also be associated with synthetic lipid membranes as described for the glycoproteins, above.

In addition to treatment of demyelinating diseases, isolated LHR (e.g., LHR-IgG) can be used for diagnosis or monitoring the state of the disease. For instance, by measuring the increase or decrease in the number of demyelinated plaques it is possible to determine whether a particular therapeutic regimen aimed at ameliorating the disease is effective.

For in vivo diagnostic imaging, radioisotopes are typically used in accordance with well known techniques. The radioisotopes may be bound to LHR either directly or indirectly using intermediate functional groups well known to those skilled in the art. For instance, chelating agents such as diethylenetriaminepentacetic acid (DTPA) and ethylenediaminetetraacetic acid (EDTA) and similar molecules have been used to bind proteins to metallic ion radioisotopes.

LHR can also be labeled with a paramagnetic isotope for purposes of in vivo diagnosis, as in magnetic resonance imaging (MRI) or electron spin resonance (ESR).

In general, any conventional method for visualizing diagnostic imaging can be used. Usually gamma and positron emitting radioisotopes are used for camera imaging and paramagnetic isotopes are used for MRI.

Immunoglobulins which recognize either LHR or its ligands can also be used to block LHR-myelin interactions. For instance, TQ1 and LAM 1.4 are monoclonal antibodies that react with human LHR and effectively interfere with lymphocyte attachment to HEV (Tedder, et al. *J. Immunol.,* 144:532 (1990), which is incorporated herein by reference). Other monoclonal antibodies known to bind human LHR include Leu-8 (Cameriai et al., *Nature* 342:78-82 (1989), which is incorporated herein by reference) and the DREG antibodies (Kishimoto et al., *PNAS* 87:2244-2248 (1990), which is incorporated herein by reference). Leu-8 is commercially available through Becton Dickonson.

The multitude of techniques available to those skilled in the art for production and manipulation of various immunoglobulin molecules can thus be readily applied to inhibit adhesion of leukocytes to myelin sheaths. As used herein, the term "immunoglobulin" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. Immunoglobulins may exist in a variety of forms besides antibodies, including for example, Fv, Fab, and F(ab)$_2$, as well as in single chains (e.g., Huston et al., *Proc. Nat. Acad. Sci. U.S.A.* 85:5879-5883 (1988) and Bird et al., *Science* 242:423-426 (1988), and Hunkapiller and Hood, *Nature* 323:15-16 (1986), which are incorporated herein by reference). For a general review of immunoglobulin structure and function see, *Fundamental Immunology,* 2d Ed., W. E. Paul ed., Ravens Press, N.Y., (1989) which is incorporated herein by reference.

Antibodies which bind either LHR or its ligands may be produced by a variety of means. The production of non-human monoclonal antibodies, e.g., murine, lagomorpha, equine, etc., is well known and may be accomplished by, for example, immunizing the animal with a preparation containing LHR or the appropriate ligand. Antibody-producing cells obtained from the immunized animals are immortalized and screened, or screened first for the production of antibody which inhibits the interaction of the myelin sheath with LHR and then immortalized. For a discussion of general procedures of monoclonal antibody production see Harlow and Lane, *Antibodies, A Laboratory Manual* Cold Spring Harbor Publications, N.Y. (1988), which is incorporated herein by reference.

The generation of human monoclonal antibodies to a human antigen (in the case of LHR isolated from human tissue) may be difficult with conventional techniques. Thus, it may be desirable to transfer the antigen binding regions of the non-human antibodies, e.g., the F(ab')$_2$ or hypervariable regions, to human constant regions (Fc) or framework regions by recombinant DNA techniques to produce substantially human molecules. Such methods are generally known in the art and are described in, for example, U.S. Pat. No. 4,816,397, Ep publications 173,494 and 239,400, which are incorporated herein by reference. Alternatively, one may isolate DNA sequences which encode a human monoclonal antibody or portions thereof that specifically bind to the human LHR by screening a DNA library from human B cells according to the general protocol outlined by Huse et al., *Science* 246:1275–1281 (1989), incorporated herein by reference, and then cloning and amplifying the sequences which encode the antibody (or binding fragment) of the desired specificity.

Immunoglobulins which inhibit the binding of LHR to myelin may also be useful in the generation of anti-idiotypic immunoglobulins. Anti-idiotype immunoglobulins may be produced by, for example, immunization of an animal with the primary immunoglobulin. In the case of immunoglobulins to LHR, those anti-idiotype immunoglobulins whose binding to the primary immunoglobulin is inhibited by LHR are selected. Since both the anti-idiotypic immunoglobulin and the receptor bind the primary immunoglobulin, the anti-idiotypic immunoglobulin may represent the "internal image" of an epitope and thus may substitute for the receptor and be used, for example, as an immunogenic reagent.

The present invention specifically provides pharmaceutical compositions which are useful in treating or diagnosing the demyelinating diseases discussed above. The pharmaceutical compositions are comprised of the blocking agents together with pharmaceutically acceptable carriers. The pharmaceutical compositions can be prepared according to standard methods (see *Remington's Pharmaceutical Sciences*, Mack Publishing Co., Philadelphia, Pa., 19th ed. (1985) which is incorporated herein by reference). The pharmaceutical compositions are suitable for use in a variety of drug delivery systems. For a brief review of present methods for drug delivery, see, Langer, *Science* 249:1527–1533 (1990), which is incorporated herein by reference.

For pharmaceutical compositions which comprise the blocking agents of the present invention, the dose will vary according to, e.g., the particular agent, the manner of administration, the particular disease being treated and its severity, the overall health and condition of the patient, and the judgment of the prescribing physician. Total dosages typically range between about 1 and about 10 mg/kg, preferably about 2 to about 7 mg/kg. Since the present invention provides evidence of a mechanism for demyelinating diseases, maximization of dosage levels for inhibition of LHR-mediated adhesion can now be achieved by one of ordinary skill in the art. "Substantial inhibition" of binding for purposes of the present invention is preferably at least about 70% inhibition, preferably 80% to 90% and most preferably 95%, or more.

The pharmaceutical compositions are intended for parenteral, topical, oral or local administration, such as by aerosol or transdermally, for prophylactic and/or therapeutic treatment. The pharmaceutical compositions can be administered in a variety of unit dosage forms depending upon the method of administration. For example, unit dosage forms suitable for oral administration include powder, tablets, pills, and capsules.

Preferably, the pharmaceutical compositions are administered directly into the cerebral spinal fluid of the CNS by intrathecal injection. Thus, this invention provides compositions for which comprise a solution of the complex dissolved or suspended in an acceptable carrier, preferably an aqueous carrier. A variety of aqueous carriers may be used, e.g., water, buffered water, phosphate buffered saline, 0.4% saline, and the like. These compositions may be sterilized by conventional, well known sterilization techniques. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the complex can vary widely, i.e., from less than about 0.05%, usually at or at least about 1% to as much as 10 to 30% by weight and will be selected primarily by fluid volumes, viscosities, etc., in accordance with the particular mode of administration selected.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient.

For aerosol administration, the complexes are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides may be employed. The surfactant may constitute 0.1%–20% by weight of the composition, preferably 0.25–5%. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above may also be employed. In producing the aerosol, a container equipped with a suitable valve is filled with the appropriate propellant, containing the finely divided compounds and surfactant. The ingredients are thus maintained at an elevated pressure until released by action of the valve.

The compositions containing the blocking agents can be administered for therapeutic, prophylactic, or diagnostic applications. In therapeutic applications, compositions containing the agents, or a cocktail thereof, are administered to a patient already suffering from a disease, as described above, in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient.

In prophylactic applications, compositions containing the blocking agents, or a cocktail thereof, are administered to a patient susceptible to or otherwise at risk of a particular disease. Such an amount is defined to be a "prophylactically effective dose." In this use, the precise amounts again depend on the patient's state of health and weight.

In diagnostic applications, compositions containing the blocking agents, or a cocktail thereof, are administered to a patient suspected of having a demyelinating disease state to determine the presence of plaques associated with the disease. Alternatively, the efficacy of a particular treatment can be monitored. An amount sufficient to accomplish this is defined to be a "diagnostically effective dose." In this use, the precise amounts will depend upon the patient's state of health and the like.

Kits can also be supplied for therapeutic or diagnostic uses. Thus, the subject composition of the present invention may be provided, usually in a lyophilized form in a container. The agents, which may be conjugated to a label or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% by weight based on the amount of blocking agent and usually present in total amount of at least about 0.001% by weight based again on the protein concentration. Frequently, it will be desirable to include an inert extender or excipient to dilute the active ingredients, where the excipient may be present in from about 1 to 99% by weight of the total composition. Where an antibody is employed, this will usually be present in a separate vial. The antibody is typically conjugated to a label and formulated according to techniques well known in the art.

The following examples are offered by way of illustration, not by way of limitation.

EXAMPLE 1

Binding of LHR-IgG to Myelinated Regions of CNS

This example describes immunohistochemical staining of CNS using LHR-IgG. The method was as modified from Watson, et al., *J. Cell Biol*, supra. Briefly, cryostat-cut tissue sections (10 μm) were fixed with 0.5% paraformaldehyde in 0.1M sodium cacodylate (pH 7.3) for 20 minutes on ice, followed by immersion in 100% methanol with 0.3% $H_2O_2$ for 20 minutes on ice. The sections were washed in Dulbecco's PBS (PBS) and incubated for 80 minutes on ice with 30 μg/ml LHR-IgG in PBS with 5% normal horse serum and 5% normal rat serum. They were then washed and incubated with biotinylated-goat anti-human IgG (Zymed Laboratories, South San Francisco, Calif.) in PBS containing 5% normal mouse serum for 30 minutes at room temperature followed by an ABC Elite reagent (Vector Labs, Burlingame, Calif.), and then AEC peroxidase substrate (Biomeda, Foster City, Calif.). Finally, the sections were counterstained with aqueous hematoxylin (Biomeda). The addition of 5% normal horse serum and 5% normal rat serum was necessary to eliminate nonspecific binding of the LHR-IgG to myelin.

The above method revealed specific staining of the myelin-rich white matter tracts of both cerebellum and spinal cord. In contrast, regions having few or no myelinated fibers such as the granular and molecular layers of the cerebellum and the grey matter of the spinal cord were negative. The addition of EGTA greatly diminished specific staining, in agreement with the known calcium-dependent binding of LHR (see, Yednock et al. *J. Cell Biol.*, 104:713, supra). Staining of myelin by LHR-IgG was restricted to CNS myelin. Myelin of the peripheral nervous system was not stained. This result further supports the role of LHR in mediated demyelinating diseases restricted to the CNS.

EXAMPLE 2

Effects of Antibodies, EGTA, and Carbohydrates on Lymphocyte Binding to Cerebellar Myelin This example demonstrates that both antibodies directed to LHR and EGTA inhibit lymphocyte binding to cerebellar myelin. The integrins, VLA-4 ($\alpha_4\beta_1$), LPAM-1 ($\alpha_4\beta_p$) and LFA-1 ($\alpha_L\beta_2$) are known to participate in a variety of lymphocyte adhesive interactions. Therefore, function-blocking antibodies against $\alpha_4$, $\beta_1$, and $\beta_2$ were also used in the assay to test the role of these receptors in adhesion to myelin.

Lymphocyte binding assays on serial sections of mouse cerebellum and spinal cord were based on the method of Stamper and Woodruff *J. Exp. Meth* 144:828 (1976), which is incorporated herein by reference. Briefly, mouse mesenteric lymph node lymphocytes ($10^6$ cells in 100 μl in RPMI 1640 supplemented with 5% FBS and 12.5 mM Hepes) were incubated on paraformaldehyde-fixed tissue sections on ice in a gyratory shaker for 30 minutes at 80 rpm. The sections were then fixed in 2.5% glutaraldehyde and stained with toluidine blue. The appropriate antibodies were added during the 30 minute incubation period. The number of bound cells per unit area (UA) was then determined microscopically. The unit area was defined with the aid of an ocular reticle or as a defined myelin strip present on a series of contiguous sections of the cerebellum.

The results of these experiments are presented in Table 2. The number of cells bound per UA ($\pm$SEM) was derived from 3–5 replicate sections. The cells used were as follows: mouse mesenteric lymph node lymphocytes (MNL), Jurkat JS9-78 (a cloned T cell line with high expression of LHR) and human peripheral blood mononuclear leukocytes (PBL) isolated from peripheral blood of healthy volunteers using Mono-Poly Resolving Medium (Flow Laboratories, Inc., McLean, Va.).

The antibodies were used at the following concentrations: MEL-14, 5 μg/ml; PolyMEL serum (from a rabbit immunized with purified mouse LHR) 1:10, LAM1.4, 1:100; anti-$\beta_2$ ascites (Telios Pharmaceuticals, Inc., San Diego, Calif.), 1:50; anti-VLA4 (HP2/1, AMAC, Inc., Westbrook, Me.), 4 μg/ml (This antibody inhibited rat lymphocyte binding to Peyer's patch by more than 70% in an in vitro binding assay); and TQ1 (Coulter Lab, Hialeah, Fla.), 10 μg/ml. EGTA was used at 10 mM.

TABLE 1

| Experiment | Cerebellum source | Cells for binding | Reagent added | Cells bound/UA | % Change Compared to Control |
|---|---|---|---|---|---|
| 1 | mouse | MNL | none | 140.3($\pm$12.2) | |
| | | | EGTA | 11.7($\pm$1.8) | −91.7 |
| 2 | human | MNL | none | 96.7($\pm$5.5) | |
| | | | MEL-14 | 38.5($\pm$8.5) | −60.2 |
| | | | PolyMEL | 56.0($\pm$10.7) | −42.1 |
| 3 | mouse | Jurkat | none | 296.7($\pm$44.9) | |
| | | | TQ1 | 7.3(3.2) | −97.5 |
| | | | PolyMEL | 6.3($\pm$3.2) | 97.9 |
| 4 | mouse | Jurkat | none | 82.0($\pm$27.3) | |
| | | | TQ1 | 5.7($\pm$2.4) | −93.1 |
| | | | LAM1.4 | 15.0($\pm$6.5) | −81.7 |
| 5 | human | Jurkat | none | 203.5($\pm$12.0) | |
| | | | TQ1 | 8.3($\pm$3.4) | −95.9 |

TABLE 1-continued

| Experiment | Cerebellum source | Cells for binding | Reagent added | Cells bound/UA | % Change Compared to Control |
|---|---|---|---|---|---|
| | | | anti-β2 | 189.3(±5.3) | −7.0 |
| | | | anti-VLA4 | 192.8(±5.8) | −5.3 |
| | | | EGTA | 3.8(±1.5) | −98.1 |
| 6 | mouse | human PBL | none | 267.3(±67.6) | |
| | | | TQ1 | 5.0(±1.5) | −98.1 |
| | | | anti-β2 | 308.0(±19.1) | +15.2 |
| | | | anti-VLA4 | 283.0(±50.1) | +6.0 |
| | | | EGTA | 12.0(±4.0) | −95.5 |

Various carbohydrates were also tested for inhibition of human lymphocyte binding to myelinated regions in the above assays. Carbohydrates tested were PPME, mannose-6-phosphate, and fructose-1-phosphate. Complete inhibition of binding was seen by PPME at 10 ug/ml and by the monosaccharides at 10 mM. The results above show that both monoclonal antibodies that react with human LHR and carbohydrates block binding of both T cells and human PBLs to the same extent as EGTA. In addition, antibodies that react with functional regions of integrin receptors were without effect.

EXAMPLE 3

Effects of phorbol ester on Lymphocyte Binding to Cerebellar Myelin

This example demonstrates that phorbol ester (PMA) inhibits Jurkat cell binding to cerebellar myelin. PMA treatment of human lymphocytes is known to cause a rapid and almost complete shedding of LHR from the cell surface (Tedder et al., supra). Jurkat cells were incubated with PMA at 100 ng/ml for 30 minutes at 37° C. or left untreated under the same conditions. After washing, they were tested in the binding assay as described above. Numbers represent cells bound per unit area and % inhibition (±SEM). EGTA was used at 10 mM. The results presented in Table 2 below, show that PMA-induced shedding of LHR inhibited T cell binding to both human and mouse myelin sheaths. FACS analysis confirmed that PMA treatment decreased LHR expression by 87% relative to untreated cells.

TABLE 2

| Cerebellum source | Treatment of cells | EGTA | Cells bound/UA | % inhibition |
|---|---|---|---|---|
| mouse | none | − | 130.0(±19.4) | |
| | | + | 12.0(±3.7) | 90.8(±2.9) |
| | PMA | − | 10.0(±3.5) | 92.3(±2.7) |
| | | + | 4.5(±1.3) | 96.5(±1.0) |
| human | none | − | 117.0(±4.1) | |
| | | + | 2.5(±1.0) | 97.9(±0.8) |
| | PMA | − | 4.5(±0.6) | 96.2(±0.6) |
| | | + | 2.8(±0.5) | 97.6(±0.4) |

These results provide further evidence that LHR is involved in the adhesion of leukocytes to myelin. Shedding of LHR by treatment with PMA almost completely inhibited binding to myelin.

The examples above demonstrate the ability of the agents of the present invention to effectively block LHR-mediated leukocyte adhesion to myelin. For the purposes of clarity and understanding, the invention has been described in these examples and the above disclosure in some detail. It will be apparent, however, that certain changes and modifications may be practiced within the scope of the appended claims.

What is claimed is:

1. A method of treating the demyelinating effect caused by a demyelinating disease in a patient, the method comprising administering to the patient a therapeutically effective dose of a pharmaceutical composition comprising a pharmaceutically acceptable carrier and a protein blocking agent which inhibits LHR-mediated binding of leukocytes to myelin, the blocking agent being present in an amount to substantially inhibit LHR-mediated adhesion.

2. A method of claim 1, wherein the blocking agent comprises an extracellular region of an endothelial cell surface glycoprotein.

3. A method of claim 2, wherein the endothelial cell surface glycoprotein is Sgp[50] or Sgp[90].

4. A method of claim 1, wherein the blocking agent comprises an immunoglobulin.

5. A method of claim 1, wherein the blocking agent selectively binds a recognition determinant on myelin.

6. A method of claim 5, wherein the blocking agent comprises an isolated LHR.

7. A method of claim 5, wherein the blocking agent comprises an LHR component and an immunoglobulin component.

8. A method of claim 1, wherein the demyelinating disease is multiple sclerosis.

9. A method of blocking LHR-mediated adhesion of leukocytes to myelin in a patient, the method comprising administering to the patient a therapeutically effective dose of a pharmaceutical composition comprising a pharmaceutically acceptable carrier and a protein blocking agent which inhibits LHR-mediated binding.

10. A method of claim 9, wherein the blocking agent comprises an immunoglobulin.

11. A method of claim 9, wherein the blocking agent selectively binds a recognition determinant on myelin.

12. A method of claim 11, wherein the blocking agent comprises an isolated LHR.

13. A method of claim 11, wherein the blocking agent comprises an LHR component and an immunoglobulin component.

* * * * *